United States Patent [19]

Pilz et al.

[11] Patent Number: 4,713,437

[45] Date of Patent: Dec. 15, 1987

[54] SALT OF OXAALKYLENEDIAMINE WITH DICARBOXYLIC ACID, CONTAINING HYDRAZINE, PREPARATION, AND NYLON PREPARED THEREFROM

[75] Inventors: Georg Pilz, Neustadt; Gert Buerger, Mannheim; Manfred Barl, Otterstadt; Gerhard Thiel, Ludwingshafen, all of Fed. Rep. of Germany

[73] Assignee: BASF Aktiengesellschaft, Ludwigshafen, Fed. Rep. of Germany

[21] Appl. No.: 875,570

[22] Filed: Jun. 18, 1986

[30] Foreign Application Priority Data

Jun. 21, 1985 [DE] Fed. Rep. of Germany ....... 3522215

[51] Int. Cl.$^4$ ............................................. C08G 69/28
[52] U.S. Cl. ............................. 528/336; 252/188.31; 260/501.2; 528/335
[58] Field of Search ................. 528/336, 335; 260/501.2; 252/188.31

[56] References Cited

U.S. PATENT DOCUMENTS 4,165,335  8/1979  Strehler et al. .................... 528/336

*Primary Examiner*—Harold D. Anderson
*Attorney, Agent, or Firm*—Keil & Weinkauf

[57] ABSTRACT

Salts of oxaalkylenediamines of the formula I

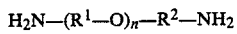

where $R^1$ and $R^2$ may be identical or different and are each alkylene of 2 to 4 carbon atoms and n is an integer from 1 to 3, and alkanedicarboxylic acids of 4 to 12 carbon atoms, terephthalic acid or isophthalic acid, which contain hydrazine, their preparation, and nylons prepared from them.

7 Claims, No Drawings

SALT OF OXAALKYLENEDIAMINE WITH DICARBOXYLIC ACID, CONTAINING HYDRAZINE, PREPARATION, AND NYLON PREPARED THEREFROM

Since nylons prepared from dicarboxylic acids and diamines have to meet high quality requirements, the same also applies to the salts obtained from dicarboxylic acids and diamines and used for the preparation of such nylons. U.S. Pat. No. 4,165,335 discloses that hydrazine hydrate is added to the alkanediamines in the preparation of salts of alkanedicarboxylic acids with alkanediamines, in order to improve the natural color. It is also known that nylons synthesized from alkanedicarboxylic acids and oxaalkylenediamines, such as 4,7-dioxadecane-1,10-diamine, can be prepared from the corresponding salts. Although very great care is taken in purifying such diamines, for example by distillation, the salts prepared from oxaalkylenediamines are unsatisfactory with regard to the required characteristics. This applies in particular to the periodate number and the UV number of the resulting salts after heat treatment. The disadvantageous properties are due to very small amounts of impurities whose nature is unknown to date and which depend on the particular method of preparation and which to date cannot be removed at an acceptable cost using the conventional purification methods.

It is an object of the present invention to provide salts of dicarboxylic acids and oxaalkylenediamines, the said salts better satisfying the set requirements with regard to their characteristics, in particular their periodate number and UV number of the salts after heat treatment, and other characteristics, and making it possible to produce nylons of improved quality.

We have found that this object is achieved by salts of oxaalkylenediamines of the formula I

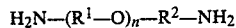

$$H_2N-(R^1-O)_n-R^2-NH_2 \qquad I$$

where $R^1$ and $R^2$ may be identical or different and are each alkylene of 2 to 4 carbon atoms and n is an integer from 1 to 3, and alkanedicarboxylic acids of 4 to 12 carbon atoms, terephthalic acid or isophthalic acid, which contain hydrazine.

We have furthermore found that salts of oxaalkylenediamines of the formula I and alkanedicarboxylic acids of 4 to 12 carbon atoms, terephthalic acid or isophthalic acid are advantageously obtained by reacting the stated starting compounds in solution if hydrazine, in the form of hydrazine hydrate, is added to the dicarboxylic acids and/or oxaalkylenediamines used as starting compounds.

The present invention furthermore relates to the use of the above salts for the preparation of nylons, and the nylons themselves prepared from these salts.

The novel salts of dicarboxylic acids and oxaalkylenediamines, containing hydrazine, have the advantage that, by a simple procedure, not only are the color number and yellow index improved but the periodate number is reduced to an unexpected extent, and the UV number of the salts after a heat treatment, as required in industry, and other characteristics are also improved.

The starting materials used are oxaalkylenediamines of the formula I

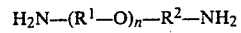

$$H_2N-(R^1-O)_n-R^2-NH_2 \qquad I$$

where $R^1$ and $R^2$ may be identical or different and are each alkylene of 2 to 4 carbon atoms. Examples of suitable alkylene radicals are ethylene, 1,2-propylene, 1,3-propylene and 1,4-butylene. Alkylene of 2 or 3 carbon atoms is particularly preferred. In formula I, n is an integer from 1 to 3, in particular 1 or 2. Examples of suitable oxaalkylenediamines are those of the formulae II to VII

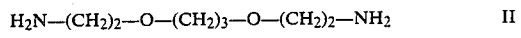

$$H_2N-(CH_2)_2-O-(CH_2)_3-O-(CH_2)_2-NH_2 \qquad II$$

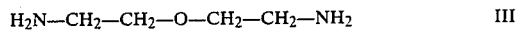

$$H_2N-CH_2-CH_2-O-CH_2-CH_2-NH_2 \qquad III$$

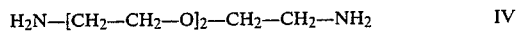

$$H_2N-[CH_2-CH_2-O]_2-CH_2-CH_2-NH_2 \qquad IV$$

$$H_2N-(CH_2)_4-O-(CH_2)_4-NH_2 \qquad V$$

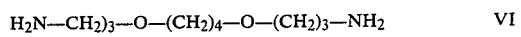

$$H_2N-(CH_2)_3-O-(CH_2)_4-O-(CH_2)_3-NH_2 \qquad VI$$

or

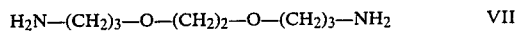

$$H_2N-(CH_2)_3-O-(CH_2)_2-O-(CH_2)_3-NH_2 \qquad VII$$

The oxaalkylenediamine of the formula VII has become particularly important industrially.

Alkanedicarboxylic acids of 4 to 12 carbon atoms are also used as starting materials. α,ω-alkanedicarboxylic acids, in particular those having a straight carbon chain, are preferred. Examples of suitable dicarboxylic acids are glutaric acid, adipic acid, suberic acid, sebacic acid and dodecanedioic acid. Adipic acid and sebacic acid have become particularly important industrially. Other suitable dicarboxylic acids are terephthalic acid and isophthalic acid and mixtures of these.

It is clear that the preferred starting materials give the preferred end products.

Salts of the stated oxaalkylenediamines and dicarboxylic acids are prepared as a rule in solution, for example in water, methanol or ethanol, in particular in aqueous solution. For example, aqueous solutions of dicarboxylic acids which are more than 40, in particular more than 50, % strength by weight are used. Such solutions are then reacted with an aqueous solution, for example a 50–60% strength by weight aqueous solution, of an oxaalkylenediamine, or with a molten oxaalkylenediamine. It is also possible to start from an aqueous solution of a diamine which advantageously is greater than 50% strength by weight, and to react this aqueous solution with a solid alkanedicarboxylic acid. The reaction is carried out, as a rule, at from 20° to 100° C., in particular from 60° to 90° C. When used in the polycondensation, the dicarboxylic acids and the diamines are of course employed in stoichiometric amounts.

For example, 50–60% strength by weight aqueous solutions of the corresponding salts of dicarboxylic acids and oxaalkylenediamines are obtained in this manner. The particular salt itself is obtained from the aqueous solution, for example by cooling and evaporation. However, it is also possible to use the aqueous solutions as obtained in the preparation directly for the preparation of nylons. Accordingly, for the purposes of the present invention, salts of dicarboxylic acids and oxaalkylenediamines are also aqueous solutions which are suitable for the preparation of nylons and which contain such salts.

An essential feature of the invention is that hydrazine, in the form of hydrazine hydrate, is added to the starting materials, ie. the dicarboxylic acids and/or oxaalkylenediamines. Advantageously, hydrazine hydrate is added to the liquid starting materials, for example the aqueous solutions of dicarboxylic acids or oxaalkylenediamines or the molten oxaalkylenediamines.

It has proven particularly advantageous to add hydrazine hydrate to the molten oxaalkylenediamines or to aqueous solutions of oxaalkylenediamines. The content of hydrazine in the form of hydrazine hydrate is advantageously kept at from 5 to 200 ppm, based on the diamine. It has proven particularly useful to add from 10 to 150 ppm of hydrazine in the form of hydrazine hydrate. It is of course clear that the particular salts of alkanedicarboxylic acids and oxaalkylenediamines contain the hydrazine added during the preparation in the form of hydrazine hydrate. The form in which hydrazine hydrate is present in the resulting salts is unknown.

The resulting salts or aqueous solutions are converted to the corresponding nylons by polycondensation, which is carried out, for example, by heating the salts or the aqueous solutions to 150°–220° C., removing the water formed and then subjecting the resulting melt to polycondensation, if appropriate under reduced pressure, at nylon-forming temperatures, in particular at from 220° to 275° C.

Nylons are useful for the production of molded materials, such as fibers, shaped articles, films and coatings.

The Examples which follow illustrate the invention.

EXAMPLE

Adipic acid in the form of a 50% strength by weight solution is reacted, at 90° C., with an equivalent amount of 4,7-dioxadecane-1,10-diamine which contains hydrazine in the form of hydrazine hydrate. The results obtained with different amounts of hydrazine are shown in the Table below.

TABLE

|  | None added | 25 ppm of hydrazine | 50 ppm of hydrazine | 100 ppm of hydrazine |
| --- | --- | --- | --- | --- |
| Natural color (1) | 7 | 5 | 4 | 2 |
| Yellowing (2) | 156 | 60 | 23 | 16 |
| UV number (3) | 446 | 374 | 273 | 227 |
| Periodate number (4) | 0.111 | 0.055 | 0.021 | 0.007 |
| UV number after 30 minutes at 90° C. | 447 | 469 | 365 | 275 |

| | |
| --- | --- |
| (1) Natural color: | APHA color number measured at 90° C. on a 40% strength by weight aqueous solution |
| (2) Yellowing: | APHA color number of a 40% strength by weight aqueous solution after heating for 24 hours at 85° C. The extinction was determined using an Elko II photometer with S 47 and J 62 filters and a path length of 5 cm. The APHA color number is obtained by subtracting extinction (J 62) from extinction (S 47) and using a calibration curve. |
| (3) UV number: | Sum of the extinctions at 226, 282 and 295 μm × 100, measured on a 40% strength by weight aqueous solution at 25° C. against doubly distilled water, using a path length of 10 cm. |
| (4) Periodate number: | 1 ml of a 0.5% strength by weight aqueous potassium periodate solution is added to 50 g of a 40% strength by weight aqueous solution of the salt, the mixture is heated for 30 minutes at 90° C. and then cooled to room temperature, and the extinction is measured with an Elko II photometer with an S 45 filter and a path length of 5 cm. |

We claim:

1. A composition comprising a salt of an oxaalkylenediamine of the formula I where $R^1$ and $R^2$

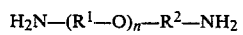

$$H_2N-(R^1-O)_n-R^2-NH_2 \qquad I$$

are identical or different and are each alkylene of 2 to 4 carbon atoms and n is an integer from 1 to 3, and an alkanedicarboxylic acid of 4 to 12 carbon atoms, terephthalic acid or isophthalic acid, and hydrazine.

2. A composition as claimed in claim 1, which contains from 5 to 200 ppm, based on oxaalkylenediamine, of hydrazine.

3. A composition comprising a salt of an oxaalkylenediamine of the formula II

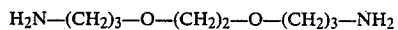

$$H_2N-(CH_2)_3-O-(CH_2)_2-O-(CH_2)_3-NH_2 \qquad II$$

and adipic acid or sebacic acid, which contains from 5 to 200 ppm, based on the diamine, of hydrazine.

4. A process for the preparation of a salt of an oxaalkylenediamine of the formula I with a dicarboxylic acid selected from the group consisting of an alkanedicarboxylic acid of 4 to 12 carbon atoms, terephthalic acid and isophthalic acid which comprises reacting the said oxaalkylenediamine with the said acid in solution, wherein hydrazine in the form of hydrazine hydrate is added to the dicarboxylic acid oxaalkylenediamine or mixtures thereof starting reactants.

5. A process as claimed in claim 4, wherein from 5 to 200 ppm, based on the oxaalkylenediamine, of hydrazine in the form of hydrazine hydrate are added.

6. A process as claimed in claim 4, wherein hydrazine in the form of hydrazine hydrate is added to the oxaalkylenediamine.

7. A nylon prepared by condensation of a salt of an oxamethylenediamine of the formula I

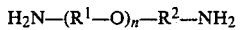

$$H_2N-(R^1-O)_n-R^2-NH_2 \qquad I$$

where $R^1$ and $R^2$ may be identical or different and are each alkylene of 2 to 4 carbon atoms and n is an integer from 1 to 3, and an alkanedicarboxylic acid of 4 to 12 carbon atoms, terephthalic acid or isophthalic acid, which contain from 5 to 200 ppm, based on the oxaalkylenediamine, of hydrazine, at nylon-forming temperatures.

* * * * *